United States Patent
Weismann

[11] Patent Number: 5,848,591
[45] Date of Patent: Dec. 15, 1998

[54] RESPIRATOR WITH OXYGEN ENRICHMENT

[75] Inventor: Dieter Weismann, Gross Grönau, Germany

[73] Assignee: Drägerwerk AG, Lubeck, Germany

[21] Appl. No.: 867,608

[22] Filed: Jun. 2, 1997

[30] Foreign Application Priority Data

Jul. 5, 1996 [DE] Germany ............ 196 27 123.1
Feb. 28, 1997 [DE] Germany ............ 197 08 094.4

[51] Int. Cl.⁶ .................................. A61M 16/00
[52] U.S. Cl. ............... 128/204.22; 128/204.24; 128/204.21; 128/205.11; 128/203.12
[58] Field of Search ............ 128/204.22, 203.28, 128/204.21, 204.24, 203.25, 203.24, 203.12, 205.11, 205.24, 204.18

[56] References Cited

U.S. PATENT DOCUMENTS

| | | |
|---|---|---|
| 2,918,917 | 12/1959 | Emerson . |
| 4,186,737 | 2/1980 | Valente et al. .......... 128/203.28 |
| 5,103,814 | 4/1992 | Mahes .................. 128/204.23 |
| 5,694,926 | 12/1997 | DeVries et al. ......... 128/206.24 |

FOREIGN PATENT DOCUMENTS

WO 87/01599  3/1987  WIPO .

*Primary Examiner*—John G. Weiss
*Assistant Examiner*—V. Srivastava
*Attorney, Agent, or Firm*—McGlew and Tuttle

[57] ABSTRACT

A respirator with a delivery device, which draws in ambient air via an inlet line and pumps it into an outlet line, with a discharge opening, which branches off from the outlet line and via which a partial flow of the gas being delivered, which can be set with a discharge valve, escapes. Oxygen is added with the smallest possible loss of gas and with good constancy of the concentration by: providing the inlet line with a buffer volume, via which the ambient air drawn in can flow; providing a return line which introduces the partial flow into the buffer volume is present between the discharge opening and the buffer volume; and providing the oxygen source connected to the inlet line and/or to the buffer volume.

15 Claims, 4 Drawing Sheets

RESPIRATOR WITH OXYGEN ENRICHMENT

FIELD OF THE INVENTION

The present invention pertains to a respirator with a delivery device which draws in breathing gas from via an inlet line and pumps it into an outlet line, with a discharge opening, which branches off from said outlet line and via which a partial flow of the gas being delivered, which can be set by means of a discharge valve, escapes, and with at least one oxygen source, which can be connected to the respirator.

BACKGROUND OF THE INVENTION

A respirator with a delivery means, which draws in ambient air via an inlet line and pumps it into a breathing tube leading to a patient, has become known from U.S. Pat. No. 2,918,917. A certain overpressure is generated with the delivery means of the prior-art respirator within the breathing tube and with the breathing mask connected to the breathing tube to support a spontaneous breathing activity of the patient. To set the overpressure, a discharge opening, which can be partially opened by means of a valve, is provided between the delivery means and the breathing tube. The breathing pressure at the breathing mask decreases or increases depending on the degree of opening of the valve and the partial gas flow being discharged via the discharge opening. The prior-art respirator operates in the so-called excess gas mode, in which the gas not needed by the patient completely escapes into the environment.

If such a respirator is to be operated with a mixture of oxygen and air, and if the oxygen is mixed in a certain percentage with the ambient air, a large portion of the gas mixture enters the environment directly via the discharge opening and thus it is no longer available to the patient for breathing.

A respirator with a turbine drawing in ambient air, which releases an oxygen-air mixture to a patient, has been known from WO 87/01 599. A line returning the breathing gas into the area in which it is drawn in by the turbine is not provided in this respirator.

SUMMARY AND OBJECTS OF THE INVENTION

The basic object of the present invention is to improve a respirator such that oxygen is mixed with the breathing gas with the smallest possible loss of gas and at good constancy of concentration.

According to the invention, a respirator is provided with a delivery means, which draws in breathing gas via an inlet line and pumps it into an outlet line. A discharge opening is provided which branches off from the outlet line. A partial flow of the gas being delivered escapes vis this discharge line. The partial flow can be set by means of a discharge valve. At least one oxygen source is provided which can be connected to the respirator. The return line is provided which extends from tile discharge opening to the outlet line and makes possible a gas flow from the discharge opening to the inlet line. The oxygen source is connected upstream of the discharge opening to the circuit formed by the inlet line, the outlet line and the return line.

The advantage of the present invention is essentially that by returning part of the breathing gas drawn in into the area of the suction side of the delivery means and by simultaneously adding oxygen from an oxygen source into the return circuit, a good possibility of setting the oxygen concentration in the breathing gas is achieved.

The delivery means is preferably set to a constant delivery capacity. However, it is also possible first to operate the delivery means with a minimum delivery capacity and then to increase the delivery capacity in a demand-adapted manner. The power consumption is reduced as a result, which prolongs the use time of the respirator in the case of battery operation.

A buffer volume is advantageously arranged in the course of the inlet line, and the return line and/or the oxygen source are connected to the buffer volume. A kind of mixing chamber is created by the buffer volume, in which there is a permanent circulation of gas due to the drawing in of ambient air by the delivery means and due to the return of part of the breathing gas being delivered. Good mixing of the ambient air with the oxygen added is achieved after a short time due to the introduction of oxygen into the buffer volume and the continuous circulation of gas. The oxygen may also be added before or after the buffer volume in the area of the inlet line, or even in the course of the return line. Based on the bypass-like deflection of the breathing gas via the return line into the buffer volume, the loss of gas is minimized compared with an arrangement with open discharge opening.

The size of the buffer volume depends on the manner in which the oxygen is added to the circuit formed by the inlet line, the outlet line and the return line and is determined by the speed with which the feed of oxygen is able to follow the variable course of the gas flow in the outlet line. If the feed of oxygen follows essentially the course of the gas flow in the outlet line, no appreciable buffer volume is needed, so that the inner volume of the delivery means, of the inlet line and of the return line is in many cases sufficient as a buffer volume. The largest buffer volume is needed, in contrast, in the case of the continuous addition of oxygen.

A control unit actuating the oxygen source is advantageously provided; this control unit is connected to a flow-measuring device which records the gas flow downstream of the discharge opening and sends a corresponding first measured signal to the control unit. Corresponding to the value of the gas flow being measured, more or less oxygen is metered into the buffer volume.

The oxygen may be metered into the buffer volume continuously and in proportion to the respiratory minute volume, in proportion to the respiratory minute volume during the inspiration, or in proportion to the breathing gas flow. In the case of metering in proportion to the breathing gas flow, there is a possibility of a strongly proportional metering or of metering with a certain time delay, i.e., somewhat lower feed of oxygen at the beginning of the inspiration and correspondingly more oxygen at the end of the inspiration.

As an alternative or in addition to the flow-measuring device, the setting of the percentage of oxygen in the breathing gas may be performed by means of an oxygen sensor in the outlet line, which sends a second measured signal to the control unit. The second measured signal is used as an additional setting variable for the oxygen source.

It is especially advantageous to design the delivery means as a turbine drive. The amount of gas needed by a patient can be drawn in from the environment with a turbine drive in a simple manner and with a good dynamic range.

The discharge valve is advantageously designed as a diaphragm valve. Such valves operate such that a certain force is admitted to the diaphragm on one side, while the other side closes a discharge opening under the action of the force. A broad dynamic range can be covered with a diaphragm valve in respiration up to frequencies of 10 Hz and higher. A flow resistance of less than 2 mbar/(L/s) (change in pressure/change in flow) can be reached in the discharge opening with such a valve. The respirator now operates as a pressure source with very low inner resistance. This is especially advantageous in pressure-based methods, e.g., CPAP, Pressure Support and BIPAP.

For using the respirator according to the present invention in anesthesia, the outlet line is designed as a breathing circuit with an inspiration line and an inspiration valve and with an expiration line with an expiration valve. To process the breathing gas exhaled by the patient, a carbon dioxide absorber is arranged in the course of the outlet line or in the expiration line, or in the return line.

To generate an anesthetic gas mixture, a laughing gas source actuated by the control unit is also provided, besides the oxygen source. The oxygen source and the laughing gas source operate as gas mixers in order to release a predetermined oxygen-to-laughing gas ratio via an anesthetic evaporator to the circuit formed by the inlet line, the outlet line, and the return line. A predetermined amount of anesthetic vapor is fed into the oxygen-laughing gas mixture by means of the anesthetic evaporator.

One exemplary embodiment of the present invention is shown in the drawing and will be explained in greater detail below.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
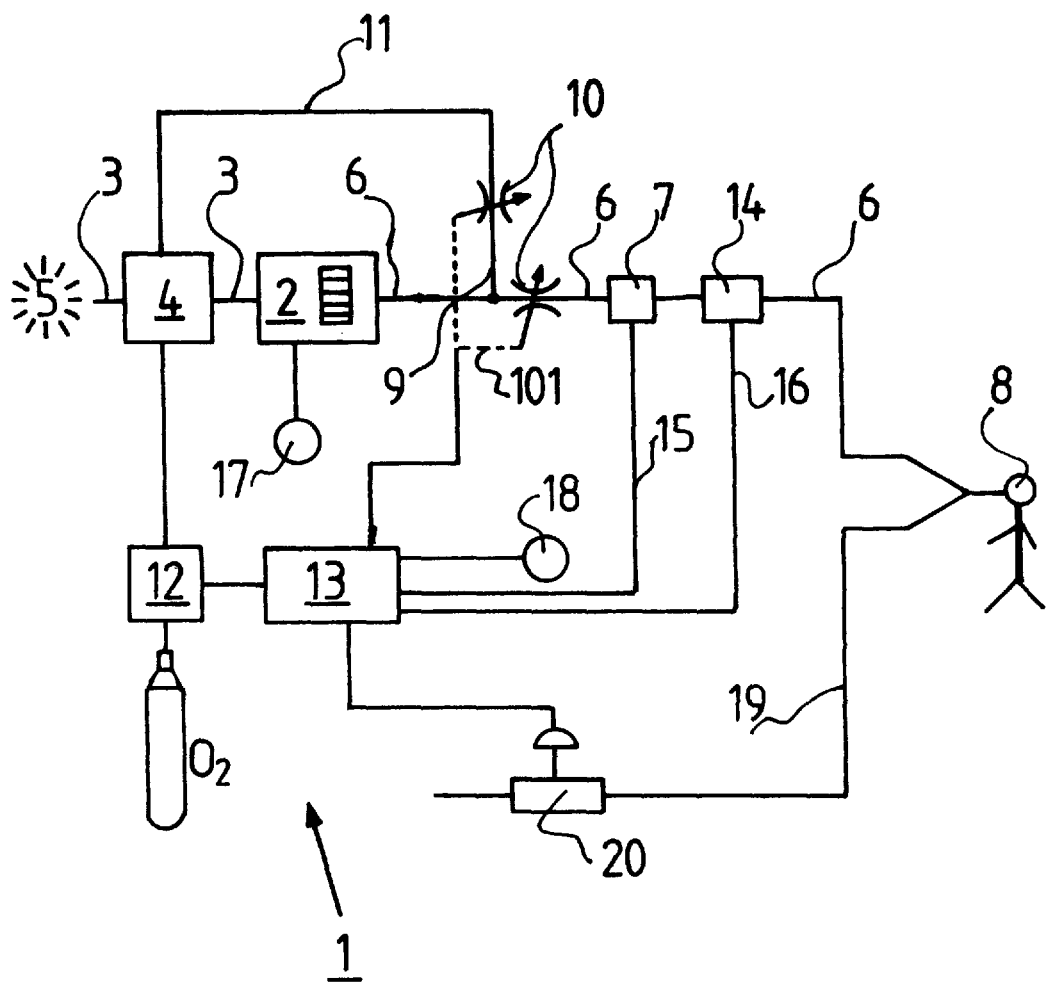
FIG. 1 is a first respirator according to the invention.

Referring to the drawings in particular, FIG. 1 schematically shows a first respirator 1, in which air is drawn in from the environment 5 by means of a delivery means 2 via an inlet line 3 and a buffer volume 4 and it is fed to a patient 8 via an outlet line 6. A discharge opening 9, which is in flow connection with the buffer volume 4 via a return line 11, branches off from the outlet line 6. An adjustable valve 10 is arranged in both the outlet line 6 and the return line 11, and this valve can be actuated via a valve-setting element 101 such that the flow resistance in the return line 11 is correspondingly increased in the case of a reduction in the cross section in the outlet line 6. An oxygen source 12, which is actuated by a control unit 13, is connected to the buffer volume 4. A flow sensor 7 and an oxygen sensor 14, which send a first measured signal proportional to the gas flow and a second measured signal proportional to the oxygen concentration, respectively, to the control unit 13 via a first line 15 and a second line 16, respectively, are arranged in the course of the outlet line 6 downstream of the discharge opening 9. The gas flow is set at the delivery means 13 with a first set point setter 17, and the desired oxygen concentration is set at the control unit 13 with a second set point setter 18. The gas exhaled by the patient 8 is released into the environment 5 via an expiration line 19 and an expiration valve 20 that can be driven by the control unit 13.

The mode of operation of the first respirator 1 according to the present invention is as follows.

The maximum gas flow needed by the patient is set at the delivery means 2 with the first set point setter 17. For this purpose, the delivery means draws air from the environment 5 via the inlet line 3 and the buffer volume 4 and pumps the gas into the outlet line 6.

The oxygen concentration desired for the respiration is entered into the control unit 13 with the second set point setter 18. The control unit 13 is also connected to the valve 10 via the valve-setting element 101 in order to set the gas flow to the patient 8 as a function of a flow profile stored in the control unit 13. The actual value of the gas flow is measured with the flow sensor 7 and is compared with the preset flow profile in the control unit 13. In the case of deviations, the valve 10 in the outlet line 6 is either opened more widely or is closed even more, while the valve 10 in the return line 11 is actuated in the opposite direction compared with that in the outlet line 6, so that the gas flow in the return line 11 is reduced in the case of increased gas flow to the patient 8. The expiration valve is closed or is set to a maximum inspiration pressure during the inspiration phase. The gas flow in the outlet line 6 is interrupted with the valve 10 at the end of the inspiration, the expiration valve 20 is switched by the control unit 13 into the open position, and the patient 8 can exhale. The valve 10 in the return line 11 is fully open during the expiration phase, so that the gas drawn in by the gas delivery means 2 from the buffer volume 4 flows back in closed circuit into the buffer volume 4.

The oxygen supply is controlled such that a metering valve, not shown in FIG. 1, is actuated within the oxygen source 12 during the inspiration phase as a function of the gas flow determined with the flow sensor 7, and the oxygen is mixed with the ambient air in proportion to the measured gas flow. The oxygen concentration is monitored with the oxygen sensor 14, and the measured concentration value is displayed at the control unit 13. However, the measured value sent by the oxygen sensor 14 may also be used in the setting of the oxygen concentration by performing a presetting of metering via the flow measurement with the flow sensor 7 and a fine setting via the measurement of the oxygen concentration with the oxygen sensor 14. Control circuits of a cascade design are especially suitable for setting the oxygen concentration.

Figure 2:
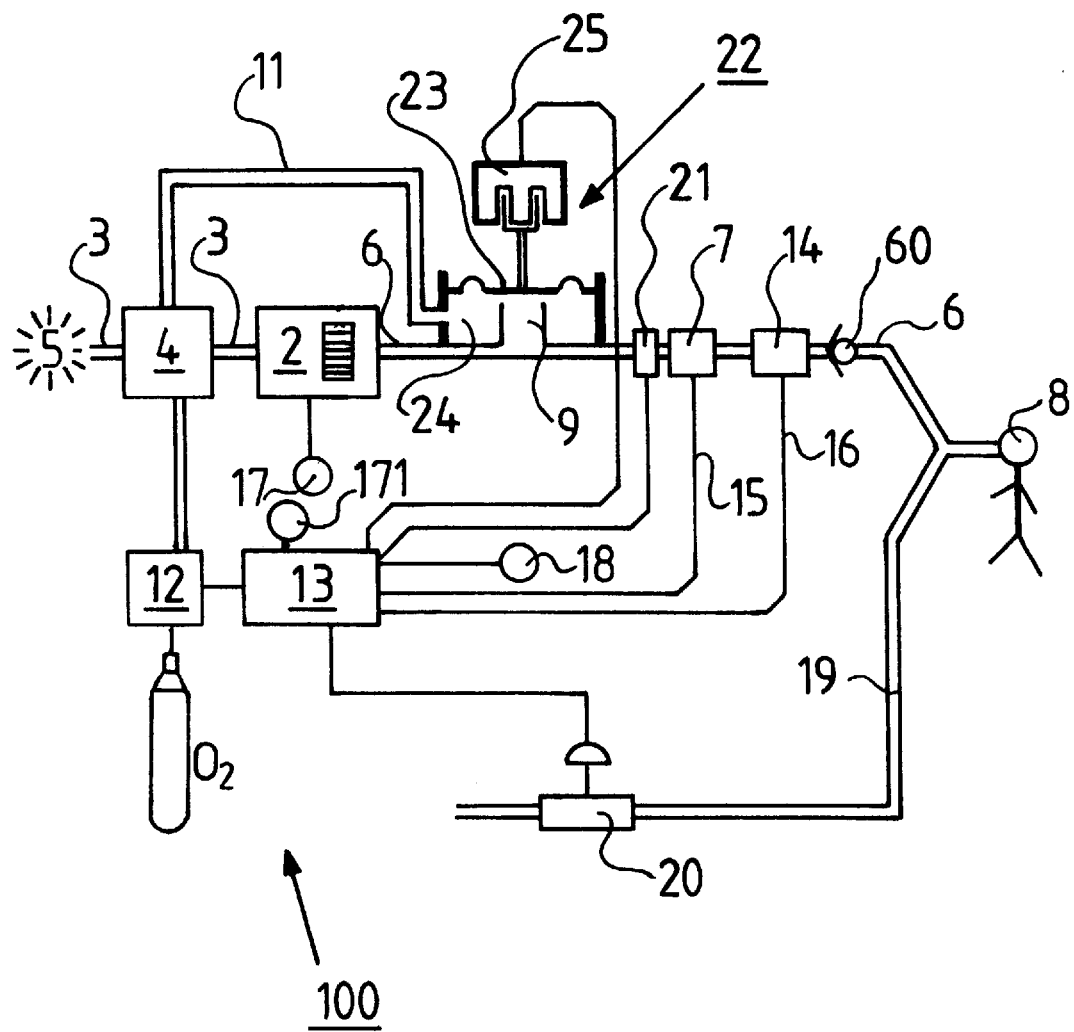
FIG. 2 is a second respirator according to the invention.

FIG. 2 schematically illustrates a second respirator 100, in which the essential change from the first respirator 1 in FIG. 1 is that the valve 10 was replaced with a diaphragm valve 22 in the outlet line 6. Identical components are designated with the same reference numbers as in FIG. 1.

While a flow-controlled respiration was achieved with the first respirator 1, the second respirator 100 is preferably used to carry out a pressure-controlled respiration. The diaphragm valve 22 comprises a diaphragm chamber 24 closed by a diaphragm 23, into which the discharge opening 9 and the return line 11 open. The discharge opening 9 can be closed with the diaphragm 23, which is actuated by a linear drive 25 connected to the control unit 13. With the diaphragm valve 22 open, there is a gas connection between the discharge opening 9 and the return line 11.

A pressure set point is sent to the control unit with a pressure set point setter 171 to carry out the pressure-controlled respiration. The diaphragm 23 is pressed by the linear drive 25 against the discharge opening 9 with a predetermined force. This force is determined by the pressure set point and the cross-sectional area of the discharge opening 9. If the pressure in the discharge opening 9 drops below the pressure set point, the diaphragm valve 22 closes more and sends more gas into the outlet line 6. In contrast, if the pressure in the discharge opening 9 increases above the pressure set point, the diaphragm valve 22 opens more widely and sends more gas into the return line 11. The gas escaping via the discharge opening 9 flows back into the buffer volume 4 via the return line 11. To compensate possible variations in pressure, the pressure in the outlet line 6 can be additionally measured with a pressure sensor 21 behind the diaphragm valve 22 during the inspiration phase, and the measured value can be included in the calculation of the predetermined force for the linear drive 25 within the control unit 13. The expiration valve 20 is closed during the inspiration phase and is opened by the control unit 13 at the beginning of the expiration. The diaphragm valve 22 is completely opened at the same time at the beginning of the expiration in order to interrupt the gas flow to the patient 8. The gas being delivered by the delivery means 2 is then sent from the discharge opening 9 directly into the buffer volume 4 via the diaphragm chamber 24 and the return line 11. A nonreturn valve 60 prevents gas from flowing back into the delivery means 2 during the expiration. The control unit 13 contains a timer, not shown in the figures, with which the inspiration and expiration phases are set. The expiration valve 20 is illustrated in FIGS. 1 and 2 as a valve that can be electrically actuated by the control unit 13. As an alternative, it is possible to drive the expiration valve pneumatically via the pressure building up in the outlet line during the inspiration phase and to close it during the inspiration phase. This valve drive, called self-drive, is described in, e.g., DE 41 42 295 C2 based on the example of a pneumatically drivable feed valve.

Figure 3:
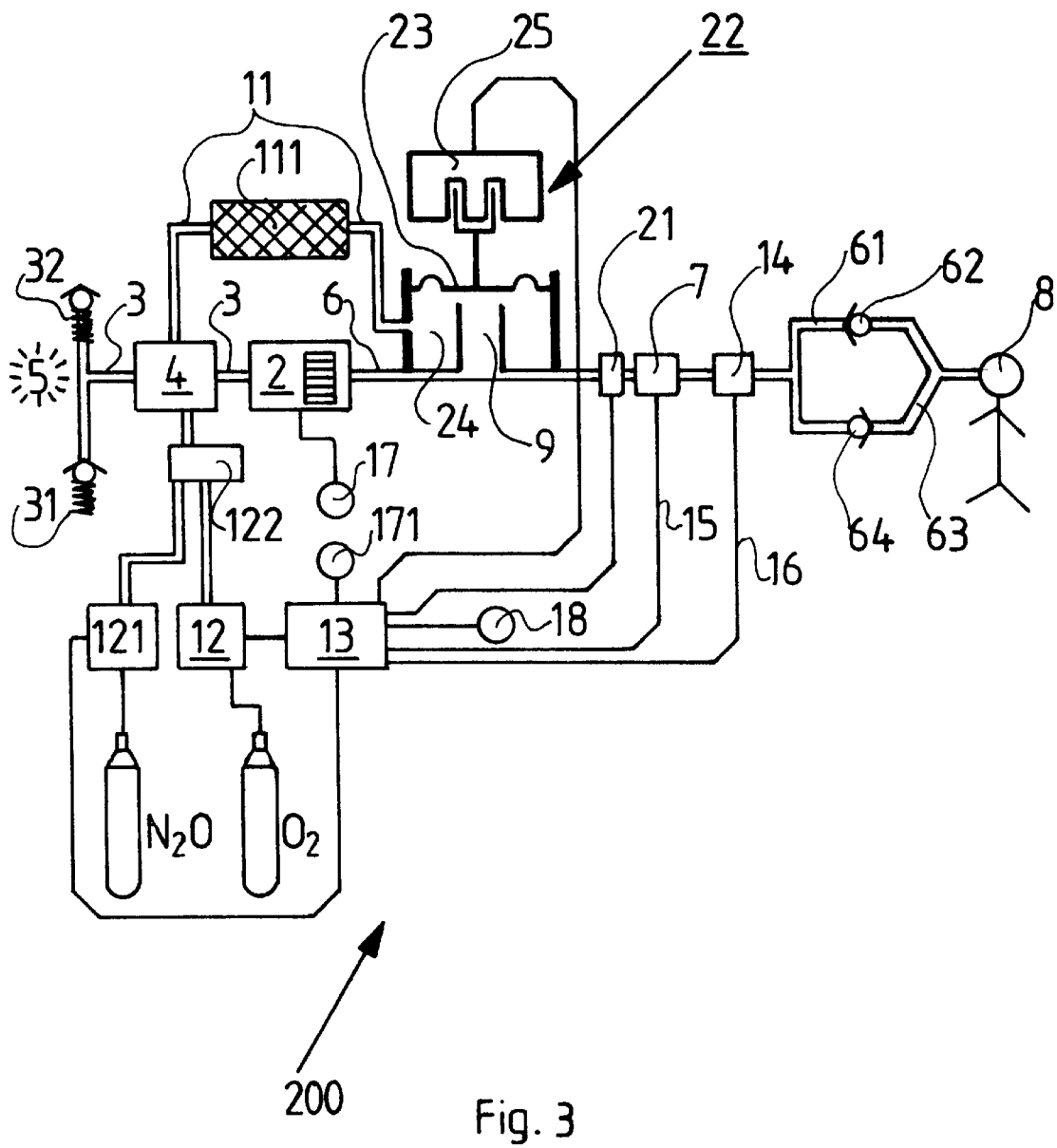
FIG. 3 is a third respirator according to the invention.

FIG. 3 shows schematically a third respirator 200, in which the essential change from the second respirator 100 in FIG. 2 is that the outlet line 6 is designed as a breathing circuit with an inspiration line 61 with an inspiration valve 62 and with an expiration line 63 with an expiration valve 64. Such an arrangement is suitable for performing inspiration anesthesia. Identical components are designated with the same reference numbers as in FIG. 2. To prepare the breathing gas, especially to remove carbon dioxide, a carbon dioxide absorber 111 is arranged in the return line 11. The inlet line 3 starting from the buffer volume 4 is closed against the environment 5 by a pressure relief valve 31 and a vacuum valve 32. In addition to oxygen, laughing gas is metered into the buffer volume 4 by means of a laughing gas source 121 that can be actuated from the control unit 13. The sources 12, 121 operate as gas mixers with a laughing gas to oxygen concentration ratio predetermined by the control unit 13. In the case of deficiency of gas in the buffer volume 4, air can be drawn in from the environment 5 via the vacuum valve 32, and excess gas can escape through the pressure relief valve 31. The laughing gas-to-oxygen gas mixture is passed through an anesthetic evaporator 122 and is enriched with anesthetic vapor in the known manner.

To carry out an inspiration stroke, the discharge opening 9 is closed with the diaphragm 23, and the gas drawn in by the delivery means 2 from the buffer volume 4 flows to the patient 8 via the inspiration line 61. The discharge opening 9 is released by the diaphragm 23 during the expiration, and the gas exhaled by the patient 8 via the expiration line 63 flows into the buffer volume 4 via the discharge opening 9, the return line 11, and the carbon dioxide absorber 111. The buffer volume 4 is preferably designed as an elastic bellows and should be dimensioned such that at least the gas volume of a maximum breathing stroke can be stored in it.

Figure 4:
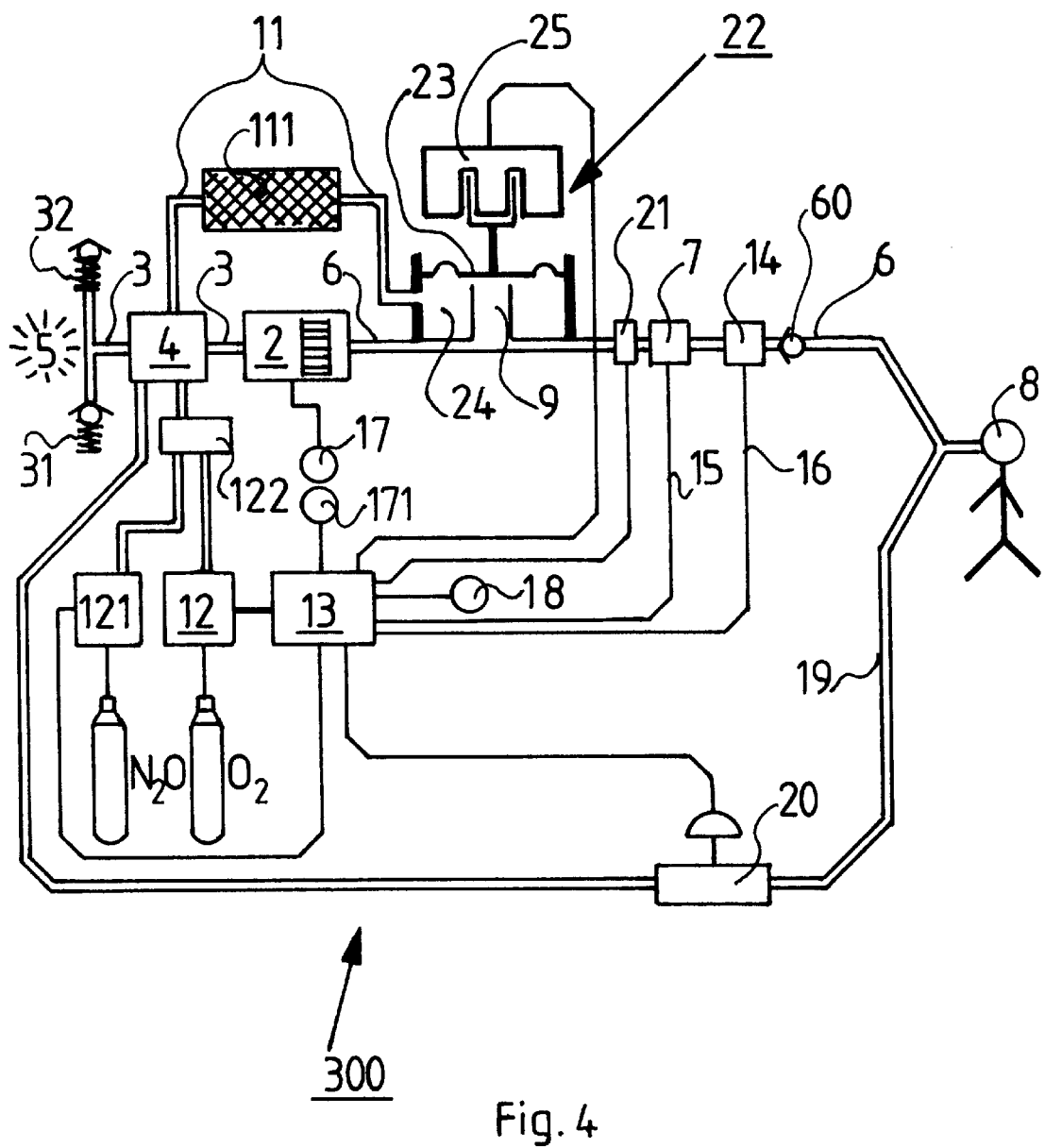
FIG. 4 is a fourth respirator according to the invention.

FIG. 4 shows schematically a fourth respirator 300, which is suitable for carrying out inspiration anesthesia and in which the essential change from the third respirator 200 according to FIG. 3 is that the gas exhaled by the patient 8 flows back into the buffer volume 4 via the expiration line 19. Identical components are designated with the same reference numbers as in FIG. 3. The breathing gas is to be prevented with the nonreturn valve 60 from flowing back into the diaphragm valve 22 or into the delivery means 2 during the expiration.

While specific embodiments of the invention have been shown and described in detail to illustrate the application of the principles of the invention, it will be understood that the invention may be embodied otherwise without departing from such principles.

What is claimed is:

1. A respirator, comprising:
   an inlet line;
   an outlet line;
   a delivery means for drawing in breathing gas via said inlet line and for pumping the breathing gas into said outlet line;
   a discharge opening which branches off from said outlet line;
   a discharge valve for setting a partial flow of the gas being delivered through said discharge opening;
   a return line extending from said discharge opening to said outlet line for passage of said partial flow from said discharge opening to said inlet line;
   an oxygen source connected to a circuit formed by said inlet line, said outlet line and said return line, upstream of said discharge opening.

2. The respirator in accordance with claim 1, further comprising a buffer volume provided in a course of said inlet line.

3. The respirator in accordance with claim 2, wherein one of said return line and said oxygen source are connected to said buffer volume.

4. The respirator in accordance with claim 1, further comprising: a control device actuating said oxygen source.

5. The respirator in accordance with claim 1, further comprising: a flow-measuring device connected to said outlet line downstream of said discharge opening.

6. The respirator in accordance with claim 5, further comprising: a control device actuating said oxygen source wherein said flow-measuring device is connected to said control unit and sends a flow measured signal for influencing actuation of said oxygen source.

7. The respirator in accordance with claim 4, further comprising an oxygen sensor disposed in a course of said outlet line connected to said control device for sending an oxygen measured signal for influencing actuation of said oxygen source.

8. The respirator in accordance with claim 1, wherein said delivery means is a turbine drive.

9. The respirator in accordance with claim 1, wherein said discharge valve is a diaphragm valve influencing the gas flow from the said discharge opening.

10. The respirator in accordance with claim 1, wherein said outlet line includes a breathing circuit with an inspiration line and with a inspiration valve and with an expiration line with an expiration valve.

11. The respirator in accordance with claim 10, further comprising: a carbon dioxide absorber arranged in a course of one of said outlet line, an expiration line and said return line.

12. The respirator in accordance with claim 4, further comprising a drivable laughing gas source connected to said circuit formed by said inlet line, said outlet line and said return line, upstream of said discharge opening.

13. The respirator in accordance with claim 12, wherein said oxygen source and said laughing gas source are provided with a gas mixer for delivering a predetermined laughing gas-to oxygen ratio, and an anesthetic evaporator is provided downstream of said oxygen source and/or said laughing gas source.

14. The respirator in accordance with claim 2, wherein said buffer volume is designed as an elastic bag.

15. The respirator in accordance with claim 10, wherein said expiration line is connected as an expiration line to said buffer volume and/or to said inlet line.

* * * * *